US011933519B2

United States Patent
Umemura et al.

(10) Patent No.: US 11,933,519 B2
(45) Date of Patent: Mar. 19, 2024

(54) AIR CONDITIONER

(71) Applicant: DAIKIN INDUSTRIES, LTD., Osaka (JP)

(72) Inventors: Futoshi Umemura, Osaka (JP); Ryuji Seino, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 18/221,487

(22) Filed: Jul. 13, 2023

(65) Prior Publication Data

US 2023/0349572 A1    Nov. 2, 2023

Related U.S. Application Data

(63) Continuation of application No. PCT/JP2022/001050, filed on Jan. 14, 2022.

(30) Foreign Application Priority Data

Feb. 18, 2021   (JP) .................................. 2021-024287

(51) Int. Cl.
*F24F 8/10*    (2021.01)
*F24F 8/22*    (2021.01)

(52) U.S. Cl.
CPC . *F24F 8/22* (2021.01); *F24F 8/10* (2021.01)

(58) Field of Classification Search
CPC ...... F24F 8/10; F24F 8/22; F24F 3/161; F24F 2011/0005; A61G 10/005
USPC ................. 55/385.2, 471; 96/224, 397, 421
See application file for complete search history.

(56) References Cited

U.S. PATENT DOCUMENTS

| | | | | |
|---|---|---|---|---|
| 5,152,814 A | * | 10/1992 | Nelson | F24F 3/167 55/385.2 |
| 5,925,320 A | * | 7/1999 | Jones | A61L 2/10 55/327 |
| 8,343,244 B2 | * | 1/2013 | Sakashita | B08B 9/035 55/296 |
| 2002/0121196 A1 | * | 9/2002 | Thakur | B01D 46/62 96/417 |
| 2011/0027137 A1 | * | 2/2011 | Kim | B01D 46/10 422/198 |
| 2015/0064069 A1 | | 3/2015 | Yi et al. | |
| 2019/0030202 A1 | | 1/2019 | Yi et al. | |

FOREIGN PATENT DOCUMENTS

| | | |
|---|---|---|
| JP | 2000-167353 A | 6/2000 |
| JP | 2002-126056 A | 5/2002 |
| JP | 2004-166996 A | 6/2004 |

(Continued)

OTHER PUBLICATIONS

International Search Report (PCT/ISA/210) issued in PCT/JP2022/001050 dated Mar. 29, 2020.

(Continued)

*Primary Examiner* — Minh Chau T Pham
(74) *Attorney, Agent, or Firm* — BIRCH, STEWART, KOLASCH & BIRCH, LLP

(57) ABSTRACT

An air conditioner includes a filter and an irradiation unit that irradiates the filter with ultraviolet light. An optical axis of the ultraviolet light emitted from the irradiation unit is inclined relative to a plane orthogonal to a thickness direction of the filter. This makes it possible to efficiently disinfect the filter.

5 Claims, 6 Drawing Sheets

(56) References Cited

FOREIGN PATENT DOCUMENTS

| JP | 2006-280428 A | 10/2006 |
| JP | 2015-51268 A | 3/2015 |
| JP | 2018-89063 A | 6/2018 |
| KR | 10-2015-0062549 A | 6/2015 |
| KR | 10-2015-0076585 A | 7/2015 |

OTHER PUBLICATIONS

English translation of International Preliminary Report on Patentability and Written Opinion of the International Searching Authority for International Application No. PCT/JP2022/001050, dated Aug. 31, 2023.

* cited by examiner

AIR CONDITIONER

CROSS REFERENCE TO RELATED APPLICATIONS

This application is a Continuation of PCT International Application No. PCT/JP2022/001050, filed on Jan. 14, 2022, which claims priority under 35 U.S.C. § 119(a) to Patent Application No. 2021-024287, filed in Japan on Feb. 18, 2021, all of which are hereby expressly incorporated by reference into the present application.

TECHNICAL FIELD

The present disclosure relates to an air conditioner.

BACKGROUND ART

An air conditioner including a pleated filter and a plurality of light source modules is known (see, for example, JP 2006-280428 A (FIGS. 1 and 5)). The filter contains a photocatalyst that decomposes a noxious gas component and an odor component. The light source modules irradiate the photocatalyst of the filter with ultraviolet light.

In the above-described air conditioner, each light source module is formed into a vertically long shape. The light source modules are arranged behind the filter at predetermined intervals in a horizontal direction. Each light source module has a large number of light emitting diodes (LEDs) that emit ultraviolet light, the light emitting diodes being arranged at intervals in a vertical direction.

SUMMARY

An air conditioner of the present disclosure includes:
a filter; and
an irradiation unit that irradiates the filter with ultraviolet light, in which
an optical axis of the ultraviolet light emitted from the irradiation unit is inclined relative to a plane orthogonal to a thickness direction of the filter.

DESCRIPTION OF EMBODIMENT

Figure 1:
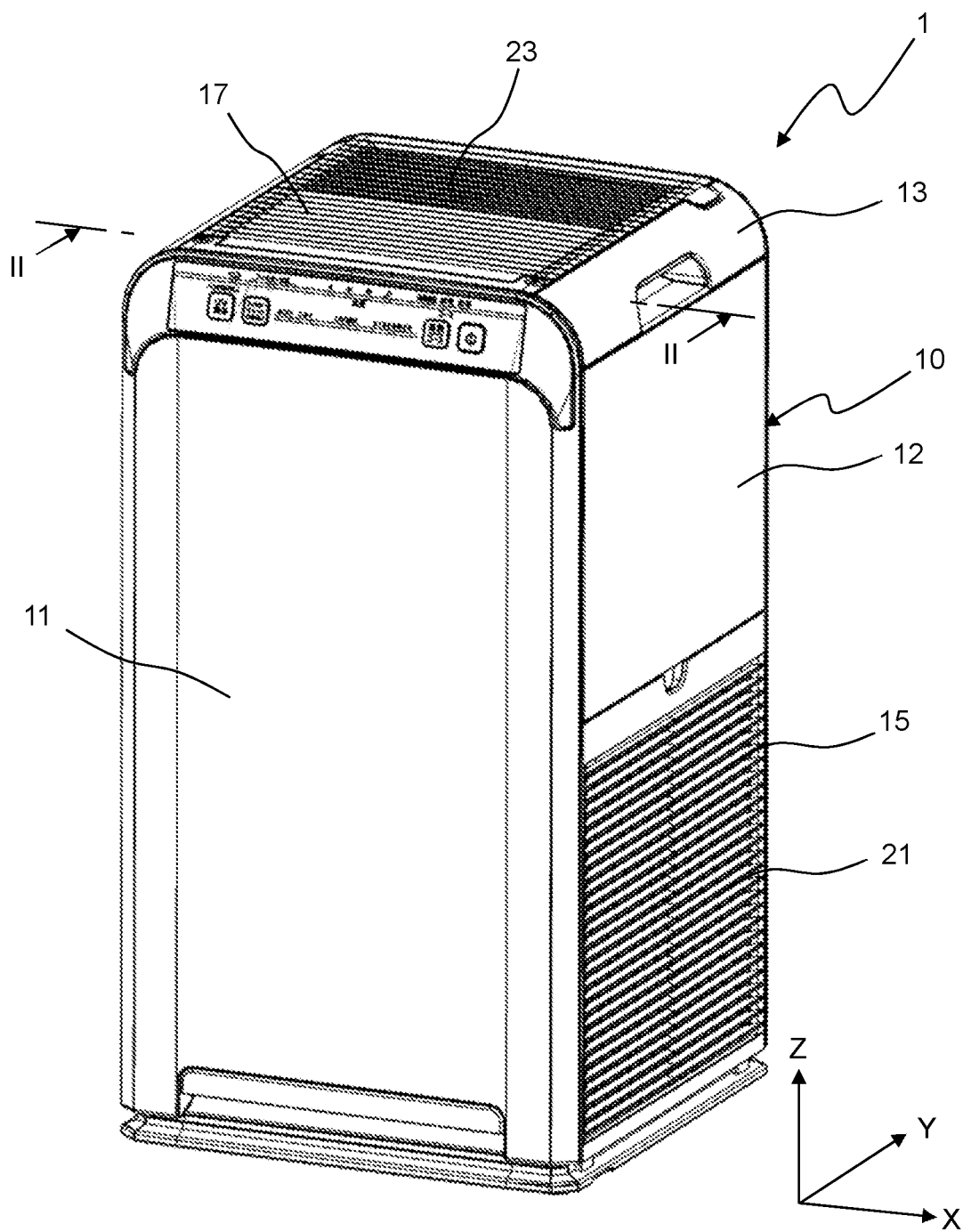
FIG. 1 is an external perspective view of an air purifier according to an embodiment of the present disclosure.

Hereinafter, an embodiment will be described. It should be noted that in the drawings, the same reference numerals represent the same or corresponding parts. In addition, the dimensions on the drawings, such as lengths, widths, thicknesses, and depths, are appropriately changed from actual scales for clarity and simplification of the drawings, and do not represent actual relative dimensions. In the drawings, a left-right direction is defined as an X-axis direction, a front-rear direction is defined as a Y-axis direction, and an up-down direction is defined as a Z-axis direction.

Figure 2:
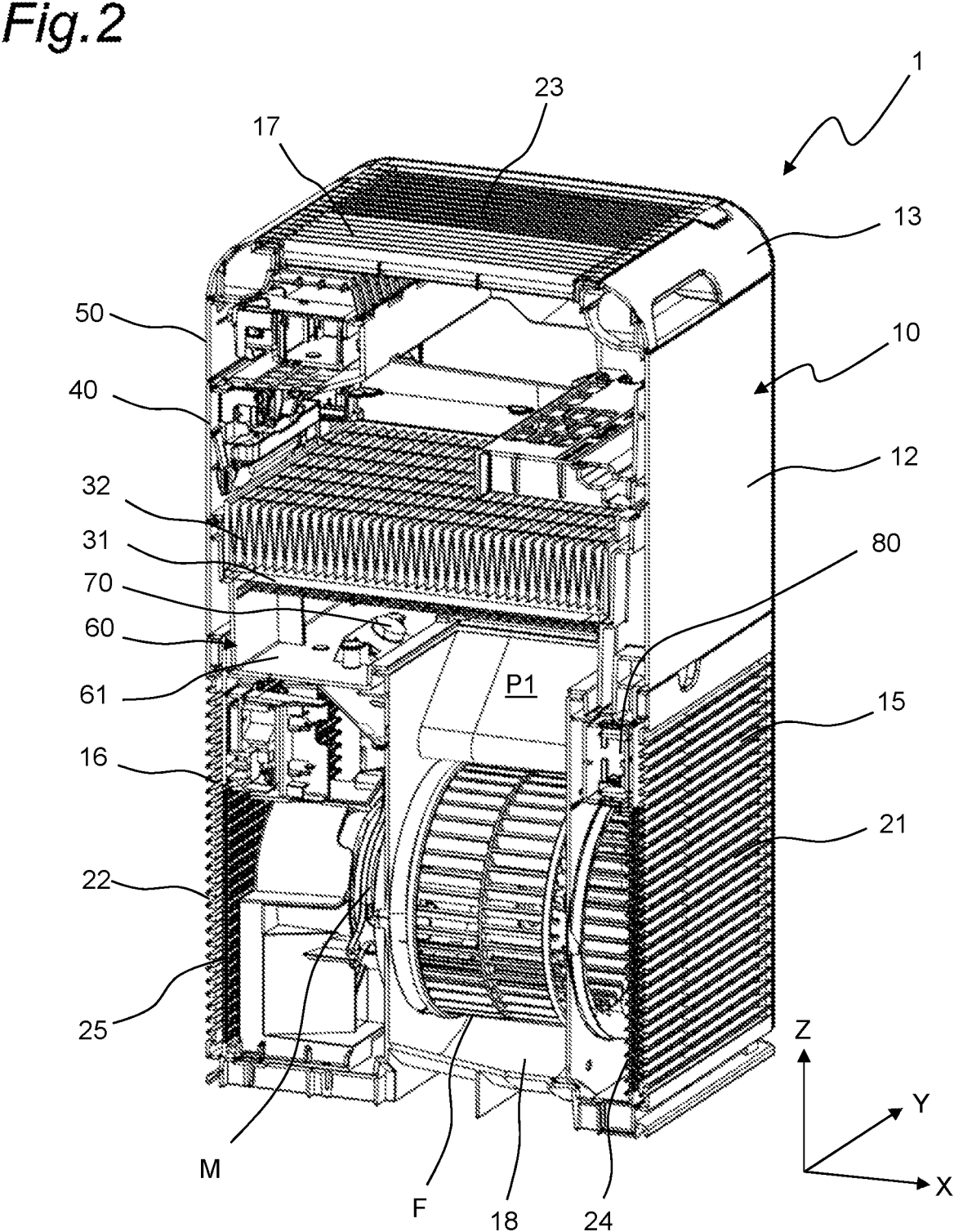
FIG. 2 is a perspective view of a cross section taken along a line II-II in FIG. 1.

FIG. 1 is an external perspective view of an air purifier 1 according to an embodiment of the present disclosure as viewed from front and obliquely above, and FIG. 2 is a perspective view of a cross section taken along a line II-II in FIG. 1. The air purifier 1 of this embodiment is an example of an air conditioner.

As illustrated in FIGS. 1 and 2, the air purifier 1 includes a casing 10 with a rectangular parallelepiped shape, a fan F, a primary filter 31, and a secondary filter 32. The casing 10 is provided with an air passage P1 having a right suction port 21, a left suction port 22, and a blow-out port 23. The fan F is disposed in the air passage P1 and blows out, through the blow-out port 23, air sucked from the right suction port 21 and the left suction port 22. The primary filter 31 is disposed in the air passage P1. The secondary filter 32 is disposed downstream of the primary filter 31 in the air passage P1.

The air purifier 1 further includes an irradiation unit 70 that irradiates an upstream surface of the primary filter 31 with ultraviolet light, and a streamer unit 80 disposed upstream of the primary filter 31 in the air passage P1. The streamer unit 80 is an example of a generation unit that generates active species.

The casing 10 includes a front panel 11, left and right side panels 12, a top panel 13, a rear panel 14 (illustrated in FIG. 5), a right suction grille 15 detachably attached below the right side panel 12, a left suction grille 16 detachably attached below the left side panel 12, and a blow-out grille 17 detachably attached to the top panel 13.

The right suction port 21 is covered with the right suction grille 15 having a grid shape so as to allow air to flow through. The left suction port 22 is covered with the left suction grille 16 having a grid shape so as to allow air to flow through. The blow-out port 23 is covered with blow-out grille 17 having a grid shape so as to allow air to flow through.

A resin case 40 to which a deodorizing filter (not illustrated) is attachable is detachably attached to the casing 10. Furthermore, an upper frame 50 is fitted into the casing 10 above the resin case 40.

Note that the casing 10 is configured to prevent the ultraviolet light from leaking out from the irradiation unit 70 provided in the casing 10 (in accordance with IEC standard 60335-2-40 (illuminance of 0.2 μW/cm 2 or less at a distance of 0.3 m from an outer contour)).

The fan F is a sirocco fan that sucks air from both sides in an axial direction and blows the air radially outward. The fan F is installed in a fan housing 18 having left and right suction ports 18a and 18b (illustrated in FIG. 3 and FIG. 4) and a scroll 18c. The fan housing 18 is provided with a blow-out port 18d through which air sucked from the suction ports 18a and 18b blows upward. A motor M is further provided, the motor M being connected to a left side of the fan F via a shaft 19 (illustrated in FIG. 4).

In the casing 10, a lower frame 60 is disposed above the fan housing 18, the lower frame 60 having a box shape and being opened upward. The lower frame 60 and the upper frame 50 form a space in which the resin case 40 is installed.

The irradiation unit 70 that irradiates the upstream surface the primary filter 31 with the ultraviolet light is attached to a bottom portion 61 of the lower frame 60. The bottom portion 61 of the lower frame 60 is an example of a partitioning member.

The primary filter 31 is a filter capable of removing particles having a particle diameter of 10 μm to 50 μm. A thickness of the primary filter 31 is set so as to allow the ultraviolet light from the irradiation unit 70 to reach a downstream surface of the primary filter 31 (for example, a thickness of about 5 mm to 10 mm). Here, the irradiation unit 70 includes a light emitting diode (LED) that emits deep ultraviolet light UV-C in a wavelength region of 100 nm to 280 nm.

Note that, in the present embodiment, the irradiation unit 70 that emits the deep ultraviolet light UV-C in the wavelength range of 100 nm to 280 nm is used, but any irradiation unit that emits ultraviolet light within a wavelength range of 100 nm to 400 nm may be used. Alternatively, an ultraviolet lamp or the like may be used as the irradiation unit.

The secondary filter 32 is a high efficiency particulate air (HEPA) filter that has a pleated structure and traps 99.97% or more of particles having a particle diameter of 0.3 μm. The secondary filter 32 is impregnated with a chemical agent exhibiting antiviral properties. For example, a lytic enzyme that destroys envelopes of viruses to inactivate viruses is used as the chemical agent.

Note that the secondary filter may be impregnated with a chemical agent exhibiting antibacterial properties to inhibit the growth of bacteria, or both the chemical agent exhibiting antiviral properties and the chemical agent exhibiting antibacterial properties may be used. Examples of the chemical agent exhibiting antiviral properties and antibacterial properties include Ag, an enzyme, ammonia, and the like, and a chemical agent containing a mixture of at least two of Ag, an enzyme, ammonia, and the like may be used.

Net-like pre-filters 24 and 25 for removing relatively large dust are attached to a leeward surface of the right suction grille 15 and a leeward surface of the left suction grille 16, respectively. The pre-filters 24 and 25 are each disposed upstream of the primary filter 31 in the air passage P1.

The air passage P1 is formed in the casing 10. Air sucked in the air passage P1 from the right suction port 21 and the left suction port 22 blows out from the blow-out port 23 via the fan F, the primary filter 31, and the secondary filter 32. The air passage P1 leads from the right suction port 21 and the left suction port 22 to the blow-out port 23.

Figure 3:
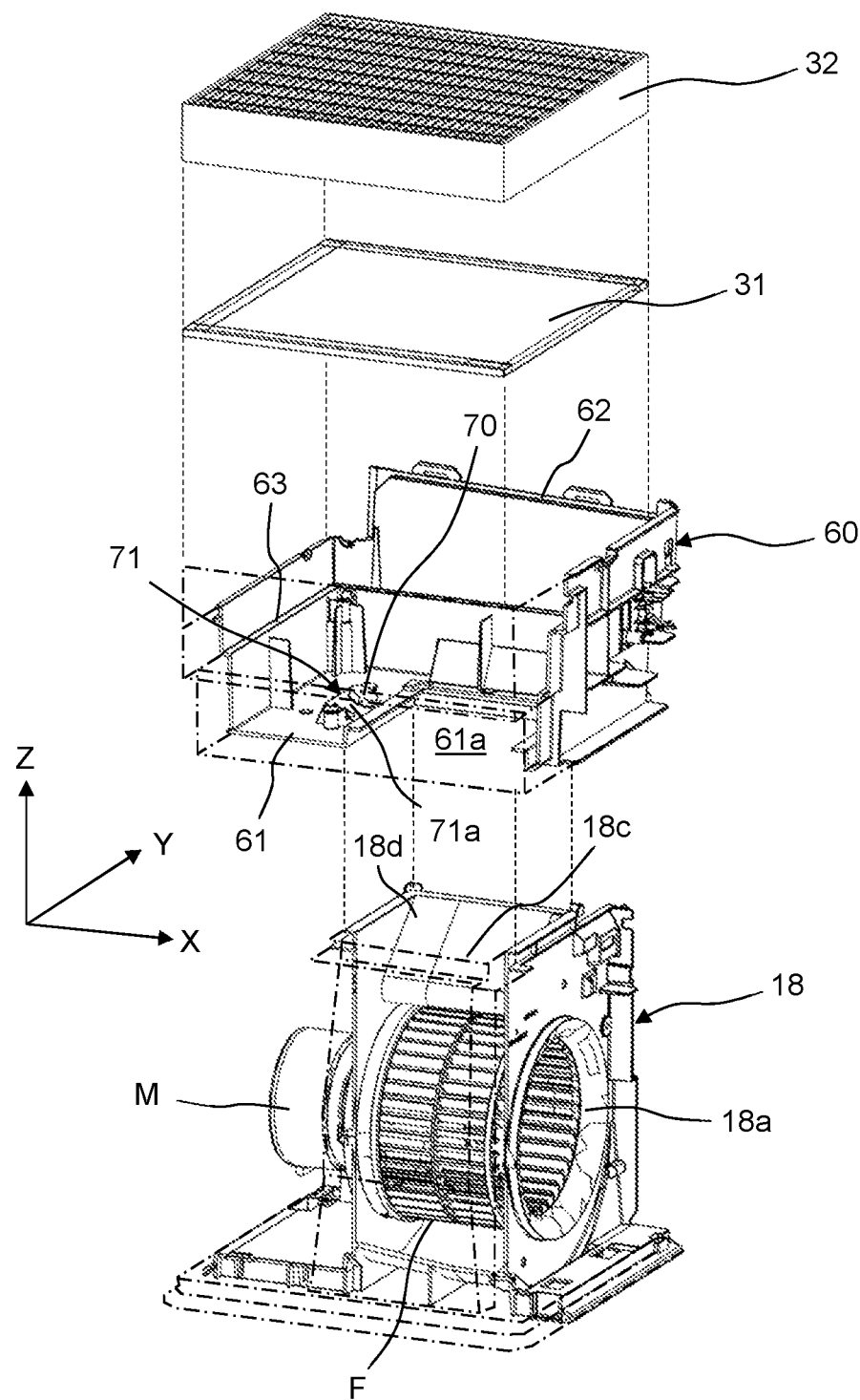
FIG. 3 is an exploded perspective view illustrating a configuration of a main part of the air purifier.

FIG. 3 is an exploded perspective view illustrating a configuration of a main part of the air purifier 1. Note that, in FIG. 3, the lower frame 60 and the fan housing 18 are each illustrated as a cross section taken along the line II-II in FIG. 1.

As illustrated in FIG. 3, the lower frame 60 includes the bottom portion 61 having an opening 61a to which the blow-out port 18d of the fan housing 18 is connected, and a wall portion 62 extending upward from an outer peripheral edge of the bottom portion 61. In the wall portion 62, a peripheral step 63 is formed at a distance from the bottom portion 61. The primary filter 31 and the secondary filter 32 are supported by an upper surface of the peripheral step 63 with the primary filter 31 and the secondary filter 32 placed on top of each other.

A base 71 having an inclined surface 71a is provided on a surface of the bottom portion 61 of the lower frame 60, the surface facing the primary filter 31. The irradiation unit 70 is attached to the inclined surface 71a of the base 71.

Figure 4:
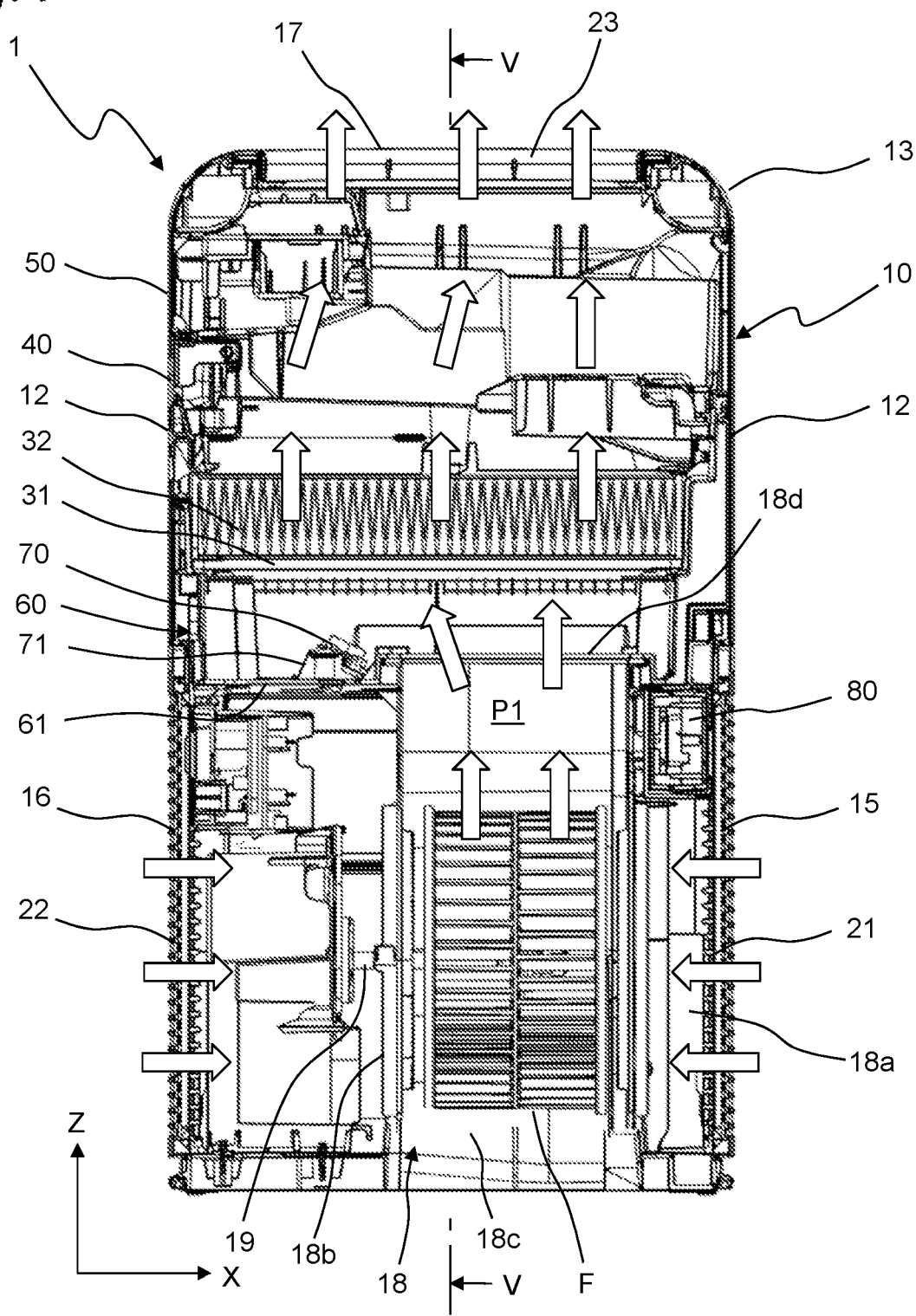
FIG. 4 is a cross-sectional view taken along the line II-II in FIG. 1.

FIG. 4 is a cross-sectional view taken along the line II-II in FIG. 1. In FIG. 4, arrows indicate the flow of air through the air passage P1.

As illustrated in FIG. 4, when the fan F is driven by the motor M, air sucked by the fan F from the right suction port 21 and the left suction port 22 blows upward from the fan F and then blows upward from the blow-out port 23 through the primary filter 31 and the secondary filter 32.

Figure 5:
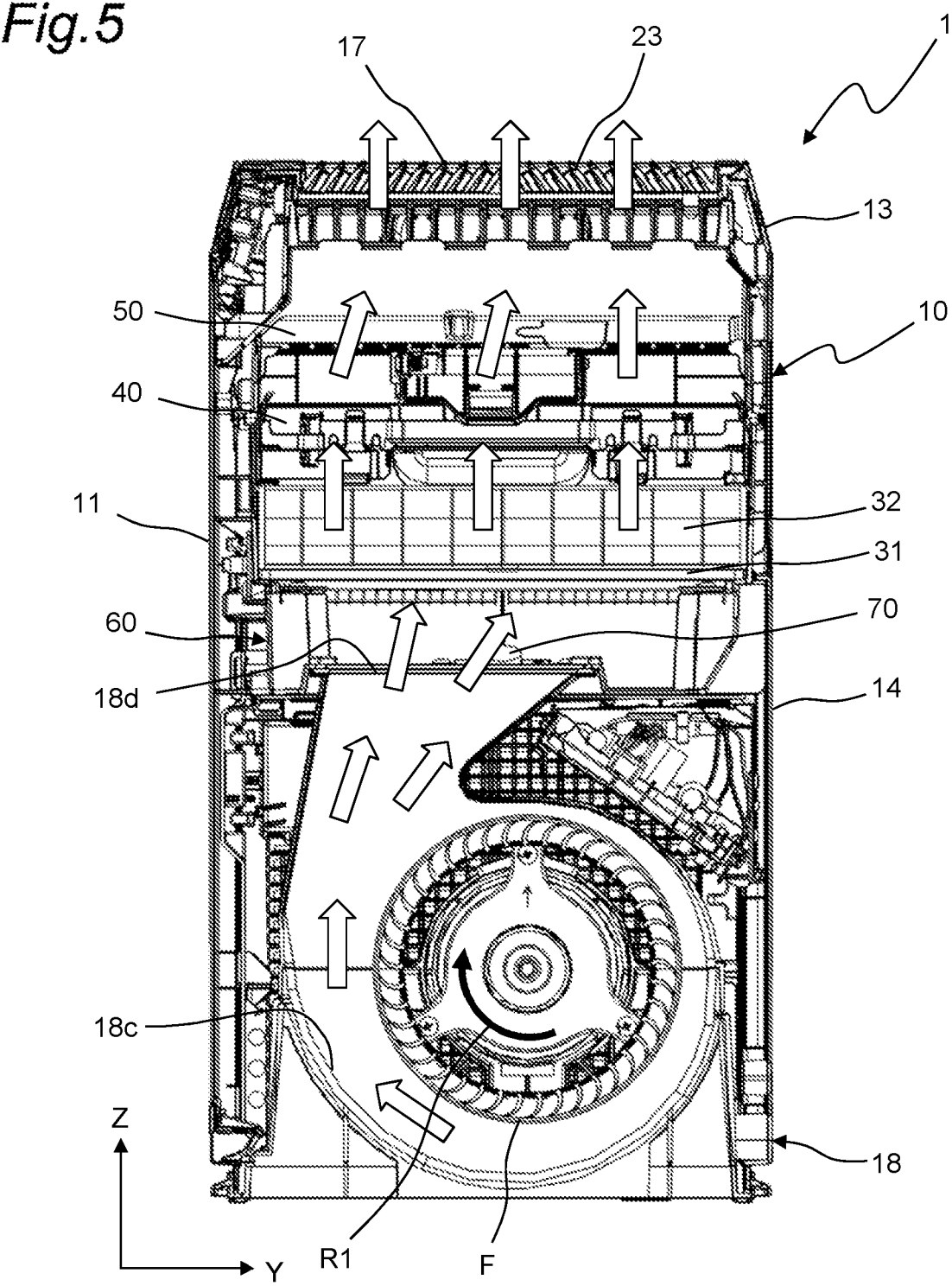
FIG. 5 is a cross-sectional view taken along a line V-V in FIG. 4.

FIG. 5 is a cross-sectional view taken along a line V-V in FIG. 4. In FIG. 5, when the fan F rotates in a clockwise direction (arrow R1), air sucked from both sides in a direction perpendicular to the paper surface blows radially outward of the fan F and is rectified by the scroll 18c of the fan housing 18 to blow upward from the blow-out port 18d.

Figure 6:
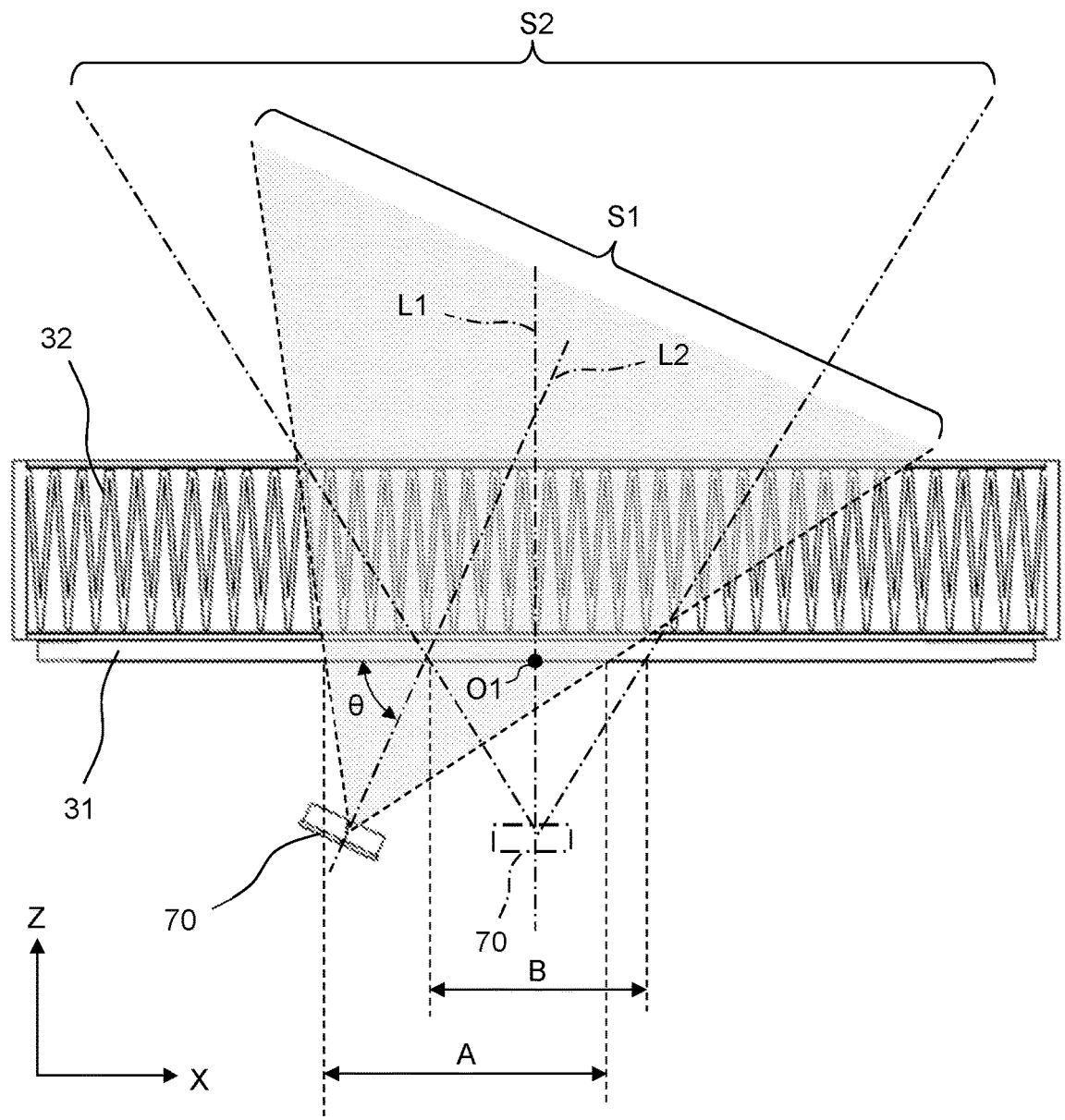
FIG. 6 is a diagram schematically illustrating an irradiation region of an irradiation unit.

FIG. 6 illustrates an irradiation region of the irradiation unit 70. As illustrated in FIG. 6, the irradiation unit 70 is disposed at a distance in the X-axis direction from a center line L1 passing through a center O1 of the primary filter 31, the center line L1 being orthogonal to the primary filter 31.

An optical axis L2 of the ultraviolet light emitted from the irradiation unit 70 is inclined relative to a plane orthogonal to a thickness direction of the primary filter 31. In the present embodiment, an angle θ formed by the optical axis L2 of the ultraviolet light emitted from the irradiation unit 70 and the plane orthogonal to the thickness direction of the primary filter 31 is about 60 degrees.

The optical axis L2 of the ultraviolet light emitted from the irradiation unit 70 passes through a center portion of the primary filter 31. Here, the center portion of the primary filter 31 is a region extending from the center O1 of the primary filter 31 toward an outer edge of the primary filter 31 by ½ or less of a distance from the center O1 to the outer edge.

The center O1 of the primary filter 31 falls within an irradiation region S1 having a relative luminous intensity in directional characteristics of the irradiation unit 70 greater than or equal to 50%. Note that a region of primary filter 31 outside the irradiation region S1 is also irradiated with ultraviolet light having a relative luminous intensity of less than 50% within a range of the directional characteristics of the irradiation unit 70. In the irradiation unit 70, a directivity angle for the irradiation region S1 is, for example, ±65 degrees, which makes a region that can be irradiated wider.

Here, with an irradiation area of the primary filter 31 in the irradiation region S1 of the irradiation unit 70 denoted as A, when the irradiation unit 70 is disposed at a position where the optical axis L2 of the irradiation unit 70 coincides with the center line L1 orthogonal to the primary filter 31, an irradiation area B of the primary filter 31 in an irradiation region S2 of the irradiation unit 70 is smaller than the irradiation area A. In the present embodiment, the irradiation area A of the primary filter 31 is about 1.6 times the irradiation area B.

As described above, in the air purifier 1 having the above-described configuration, the optical axis L2 of the ultraviolet light emitted from the irradiation unit 70 is inclined relative to the plane orthogonal to the thickness direction of the primary filter 31, so that it is possible to increase the region of the primary filter 31 irradiated with the ultraviolet light without increasing a distance in the Z-axis direction between the irradiation unit 70 and the primary filter 31, which allows efficient disinfection of the primary filter 31.

Further, the bottom portion 61 (partitioning member) of the lower frame 60 is provided upstream of the primary filter 31 and downstream of the fan F, and the irradiation unit 70 is attached to the downstream surface of the bottom portion 61 of the lower frame 60, so that the air from the fan F is prevented from directly striking the irradiation unit 70, and it is therefore possible to reduce the adhesion of dust to the irradiation unit 70.

Further, the base 71 is provided on the surface of the bottom portion 61 of the lower frame 60 facing the primary filter 31, and the irradiation unit 70 is attached to the inclined surface 71a of the base 71, so that it is possible to easily attach the irradiation unit 70 with the optical axis L2 of the irradiation unit 70 inclined relative to the plane orthogonal to the thickness direction of the primary filter 31.

Further, the air from the fan F blows out from the opening provided in the bottom portion 61 of the lower frame 60 toward the primary filter 31, so that the air from the fan F is prevented from directly striking the irradiation unit 70, and it is therefore possible to reduce the adhesion of dust to the irradiation unit 70.

Further, the ultraviolet light emitted from the irradiation unit 70 passes through the center portion of the primary filter 31, so that it is possible to irradiate the entirety of the primary filter 31 or almost the entirety of the primary filter 31 with the ultraviolet light without uneven irradiation.

Further, the irradiation unit 70 is disposed out of alignment with the center line L1 passing through the center O1 of the primary filter 31 and orthogonal to the primary filter 31, so that it is possible to prevent the irradiation unit 70 from hindering the flow of air through the primary filter 31.

Further, the center O1 of the primary filter 31 falls within the irradiation region having a relative luminous intensity in the directivity of the irradiation unit 70 greater than or equal to 50%, so that it is possible to irradiate the entirety of the primary filter 31 or almost the entirety of the primary filter 31 with the ultraviolet light without uneven irradiation.

Further, one irradiation unit 70 can irradiate the entirety of the primary filter 31 or almost the entirety of the primary filter 31 with the ultraviolet light without an increase in the distance between the irradiation unit 70 and the primary filter 31, so that it is possible to reduce the cost and the power consumption as compared with a case where a plurality of irradiation units 70 are used.

In the above-described embodiment, the air purifier 1 has been described as an example of the air conditioner, but the present disclosure may be applied to an air conditioner having a cooling function or a heating function.

In the above-described embodiment, the air purifier 1 in which the fan F is disposed upstream of the primary filter 31 and the secondary filter 32 has been described, but the fan may be disposed downstream of the primary filter and the secondary filter.

Although a specific embodiment of the present disclosure has been described, the present disclosure is not limited to the above-described embodiment, and various modifications can be made within the scope of the present disclosure.

REFERENCE SIGNS LIST 1 air purifier
10 casing
11 front panel
12 side panel
13 top panel
14 rear panel
15 right suction grille
16 left suction grille
17 blow-out grille
18 fan housing
18a, 18b suction port
18c scroll
18d blow-out port
19 shaft
21 right suction port
22 left suction port
23 blow-out port
24, 25 pre-filter
31 primary filter
32 secondary filter
40 resin case
50 upper frame
60 lower frame
61 bottom portion (partitioning member)
61a opening
62 wall portion
63 peripheral step
70 irradiation unit
71 base
71a inclined surface
80 streamer unit
F fan
M motor
P1 air passage

What is claimed is:

1. An air conditioner comprising:
a filter;
an irradiation unit that irradiates the filter with ultraviolet light;
a fan that sends air to the filter;
an air passage in which the filter is disposed and through which the air from the fan flows; and
a partitioning member provided upstream of the filter and downstream of the fan,
wherein
an optical axis of the ultraviolet light emitted from the irradiation unit is inclined relative to a plane orthogonal to a thickness direction of the filter,
the partitioning member is outside the air passage,
the partitioning member is provided with an opening through which the air from the fan blows out toward the filter, and
the irradiation unit is attached to a downstream surface of the partitioning member, the irradiation unit provided outside the opening.

2. The air conditioner according to claim 1, further comprising a base that is provided on a surface of the partitioning member facing the filter, the base having an inclined surface to which the irradiation unit is attached.

3. The air conditioner according to claim 1, wherein the optical axis of the ultraviolet light emitted from the irradiation unit passes through a center portion of the filter.

4. The air conditioner according to claim 1, wherein the irradiation unit is disposed out of alignment with a center line that passes through a center of the filter, the center line being orthogonal to the filter.

5. The air conditioner according to claim 1, wherein the number of the irradiation units is one.

* * * * *